(12) United States Patent
Murata et al.

(10) Patent No.: US 7,750,183 B2
(45) Date of Patent: Jul. 6, 2010

(54) METHODS FOR PURIFYING AMINO ACIDS

(75) Inventors: Hideki Murata, Yamaguchi (JP); Hiroshi Nagano, Yamaguchi (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 12/282,786

(22) PCT Filed: Mar. 15, 2007

(86) PCT No.: PCT/JP2007/055193

§ 371 (c)(1), (2), (4) Date: Oct. 6, 2008

(87) PCT Pub. No.: WO2007/105790

PCT Pub. Date: Sep. 20, 2007

(65) Prior Publication Data

US 2009/0054685 A1    Feb. 26, 2009

(30) Foreign Application Priority Data

Mar. 15, 2006    (JP) ............................ 2006-071579

(51) Int. Cl.
   *C07C 227/40*    (2006.01)
(52) U.S. Cl. .................................... 562/554
(58) Field of Classification Search ............. 562/554
   See application file for complete search history.

(56) References Cited

U.S. PATENT DOCUMENTS 4,714,767 A * 12/1987 Tanaka et al. ............ 548/339.1

FOREIGN PATENT DOCUMENTS

JP    9-252794    9/1997

OTHER PUBLICATIONS

Winters et al., 41 Ind. Eng. Chem., 460-63 (1949).*
Mustafa et al., 14 Langmuir, 2378 (1998).*
Search Report from corresponding European Application No. 07738643.1 dated Feb. 3, 2009.
Amberlite® IRC50, Synthetic Cation Exchange Resin, ROHM-HAAS, Product Data Sheet, 2000, available on Nov. 16, 2009 from << www.rohmhaas-polska.com/produkty/pds/amberlite/Irc50. pdf>>.
Diaion® Cation-Exchange Resins and Diaion® Ion-Exchange Resins, Mitsubishi Chemical, retrieved from <<http://www.diaion.com/Index_E.htm>> on Oct. 19, 2009 and << http://www.diaion.com/Diaion_Main/Diaion_Main_R_E.htm>> on Oct. 21, 2009.

* cited by examiner

*Primary Examiner*—Daniel M Sullivan
*Assistant Examiner*—Yevegeny Valenrod
(74) *Attorney, Agent, or Firm*—Kenneth H. Sonnenfeld; King & Spalding LLP

(57) ABSTRACT

In the method for separating and purifying a basic amino acid, preferably the basic amino acid selected from arginine, lysine or ornithine from a culture containing the amino acid, the culture containing the a basic amino acid and microbial cells, preferably the culture whose pH is 4 to 10, is charged onto the top of a column filled with a weak acid cation exchange resin whose particle size is 300 μm or more and passed therethrough, and then an eluent is poured into the column from the top thereof whereby accomplishing the separation and the purification of the basic amino acid.

6 Claims, No Drawings

METHODS FOR PURIFYING AMINO ACIDS

TECHNICAL FIELD

The present invention relates to the method for purifying a basic amino acid.

BACKGROUND ART

Known methods for separating and purifying a basic amino acid from a culture containing the basic amino acid and microbial cells using an ion exchange resin includes (1) a method in which after removing solid components such as microbial cells by centrifugation, condensing precipitation using a polymeric condensing precipitator or ultrafiltration and the like from the culture made acidic, a cell-free culture fluid is charged onto the top of a column filled with a strong acid cation exchange resin adjusted at pH0.5 to pH3.0 and then an eluent is charged onto the top of the column whereby separating and purifying the basic amino acid (Patent References 1 to 3 and the like), (2) a method in which a basic amino acid is separated using a weak acid cation exchange resin from a neutral aqueous solution containing several amino acids including the basic amino acid (Patent Reference 4) and (3) a method in which a culture containing microbial cells is charged onto the top of a column filled with a strong acid cation exchange resin to allow an amino acid to be adsorbed on the resin and then water is poured into the column backward via the bottom thereof to allow the cells depositing on the resin to float up and to be removed via the top of the column and then the amino acid is eluted (Patent Reference 5).

However, the abovementioned method (1) requires a pretreatment to remove the microbial cells from the culture before bringing the culture into contact with the ion exchange resin, and also requires an acidic pH of the culture which is 3 or lower for the purpose of removing the cells efficiently, and such a pH is not within the range of pH which allows the exchange by the weak acid ion exchange resin and the basic amino acid is adsorbed only weakly onto the weak acid ion exchange resin. Accordingly, it is not possible to separate the basic amino acid efficiently using the weak acid ion exchange resin from the acidic culture after removing the cells.

When applying the abovementioned method (2) after separating and removing the cells from the neutral culture containing the microbial cells, the purification yield is problematically poor because of poor separation of the cells in a neutral range.

Also in the abovementioned method (3), the amino acid purification efficiency is disadvantageously poor since the cells contained in the culture together with the amino acid are mostly deposited on the resin.

Patent Reference 1: Japanese Published Examined Patent Application No. 39516/1978

Patent Reference 2: Japanese Published Examined Patent Application No. 61272/1994

Patent Reference 3: Japanese Published Examined Patent Application No. 5050/1964

Patent Reference 4: U.S. Pat. No. 2,549,378

Patent Reference 5: Japanese Published Examined Patent Application No. 53509/1992

DISCLOSURE OF THE INVENTION

Problems to be Solved by the Invention

An objective of the present invention is to provide a method for purifying a basic amino acid to a high purity in an inexpensive and convenient manner from a culture containing microbial cells.

Means for Solving the Problems

The present invention relates to the following (1) to (3).

(1) A method for separating and purifying a basic amino acid from a culture comprising the amino acid, which comprises allowing a culture comprising a basic amino acid and microbial cells to be charged onto the top of a column filled with a weak acid cation exchange resin whose particle size is 300 μm or more and pass therethrough, and thereafter allowing an eluent to pass through the column, to thereby separate and purify the basic amino acid.

(2) The method according to the above (1), wherein the pH of the culture comprising the basic amino acid and the microbial cells is 4 to 10.

(3) The method according to the above (1) or (2), wherein the basic amino acid is arginine, lysine or ornithine.

EFFECT OF THE INVENTION

According to the present invention, a basic amino acid can inexpensively and conveniently be purified to a high purity from a culture containing microbial cells.

BEST MODE FOR CARRYING OUT THE INVENTION

A culture containing a basic amino acid and microbial cells according to the present invention may for example be a culture obtained by culturing a microorganism capable of producing the basic amino acid in a medium so as to form and accumulate the basic amino acid in the medium.

The microorganism mentioned above may be any microorganism capable of producing a basic amino acid, and preferably a prokaryote, more preferably a bacterium. The prokaryote may for example be microorganisms belonging to the genus *Escherichia, Serratia, Bacillus, Brevibacterium, Corynebacterium, Microbacterium, Pseudomonas, Agrobacterium, Alicyclobacillus, Anabena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* or *Zymomonas*, and specifically mention may be made of those of *Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrica, Anabaena doliolum, Anabaena flos-aquae, Arthrobacter aurescens, Arthrobacter citreus, Arthrobacter globformis, Arthro-* bacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium sp. ATCC29409, Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Zymomonas mobilis, and the like.

The preferred prokaryote may for example be the bacteria belonging to the genus Escherichia, Serratia, Bacillus, Brevibacterium, Corynebacterium, Pseudomonas or Streptomyces, more preferably bacteria belonging to the genus Corynebacterium, and those which may be exemplified are the species of the abovementioned genus Escherichia, Serratia, Bacillus, Brevibacterium, Corynebacterium, Pseudomonas or Streptomyces, and the like can be mentioned. Preferably, the species of the genus Corynebacterium can be mentioned.

Still more preferred bacteria include Escherichia coli, Corynebacterium glutamicum, Corynebacterium ammoniagenes, Corynebacterium lactofermentum, Corynebacterium flavum, Corynebacterium efficasis, Brevibacterium flavum, Bacillus subtilis, Bacillus megaterium, Serratia marcescens, Pseudomonas putida, Pseudomonas aeruginosa, Streptomyces coelicolor or Streptomyces lividans, with Corynebacterium glutamicum being particularly preferred.

As the basic amino acid in the present invention, any amino acid having a positive charge may be mentioned, and those exemplified more preferably include arginine, ornithine, lysine, and the like. The basic amino acid may be in L-form, DL-form, D-form or a mixture thereof.

The medium for culturing the microorganisms mentioned above may be any natural or synthetic medium as long as it contains carbon sources, nitrogen sources, inorganic salts, and the like which can be assimilated by the microorganism and allows the culture of the microorganism to be conducted efficiently.

The carbon sources include those capable of being assimilated by the microorganism, for example, carbohydrates such as glucose, fructose, sucrose, molasses containing these materials, starches or starch hydrolysates, organic acids such as acetic acid and the like, propionic acid, alcohols such as ethanol and propanol and the like.

The nitrogen sources include ammonia and ammonium salts of inorganic or organic acids such as ammonium chloride, ammonium sulfate, ammonium acetate, ammonium phosphate, other nitrogen-containing compounds as well as peptone, meat extracts, yeast extracts, corn steep liquor, casein hydrolysates, soy bean bran and soy bean bran hydrolysates, various cultured microbial cells and digested products thereof.

The inorganic salts include potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is conducted under aerobic condition, for example, by shaking culture, agitation submerged culture, etc. The culturing temperature is preferably 15 to 40° C., and the culturing time period is usually 6 hours to 14 days. The pH during culturing is maintained preferably at 4.0 to 10.0.

As the weak acid ion exchange resin employed in the present invention, a resin having a particle size giving a space between the particles to allow the passage of a microbial cell, preferably a prokaryotic cell, more preferably a bacterial cell, still more preferably a cell of a bacterium belonging to the genus Corynebacterium, especially a cell of Corynebacterium glutamicum may be used, and it is not essential that the particle size is uniform.

Said resin may for example be a resin whose particle size is 300 μm or more, preferably 350 μm or more, more preferably 400 μm or more, still more preferably 420 μm or more, especially preferably 500 μm or more, the most preferably 600 μm or more. The resin having the particle size mentioned above may for example be a resin obtainable by subjecting a resin whose particle size is not uniform to a sieve of a mesh size of 0.30 mm, 0.35 mm, 0.40 mm, 0.42 mm, 0.50 mm or 0.60 mm.

Although a resin employed in the invention having a particle size of 300 μm or more is not subjected to any upper limit of the particle size since a larger space between the particles make it easier for a microbial cell to pass through the particles, it is contemplated, in view of an easy handling and a better efficiency of the amino acid purification, to use a carrier containing 10% or less of particles having particle sizes of 2000 μm or more, preferably containing 10% or less of particles having particle sizes of 1500 μm or more, more preferably containing 10% or less of particles having particle sizes of 1180 μm or more.

The weak acid cation exchange resins mentioned above include acrylic acid-based or methacylic acid-based resin such as DIAION WK10, WK11, WK20 and WK40 (Mitsubishi Chemical Corporation), MAC-3 (Dow Chemical Company), CNP80, CNPLF and CNP105 (Bayer Corporation), IRC50 and IRC76 (Amberlite) as well as those obtained by adjusting the particle sizes of the same.

The method for adjusting the particle size of the resin mentioned above may for example be a method of obtaining the resin which does not pass through the sieve with the mesh size of 0.30 mm, preferably 0.35 mm, more preferably 0.40 mm, further preferably 0.42 mm, especially preferably 0.50 mm, and most preferably 0.60 mm.

The concentration of a basic amino acid in a culture upon being charged onto a column filled with a weak acid cation exchange resin is not limited particularly as long as the basic amino acid is solubilized. When a crystal of the basic amino acid is precipitated in the culture after completion of the cultureing, the basic amino acid crystal is dissolved by adding water, by heating or by adding an acid, or the basic amino acid crystal is separated off, and then the culture may be charged.

While the pH of the culture to be charged onto the column is not limited particularly, and is pH4.0 to 10.0, preferably 5.0 to 8.0, and the pH of the culture may be adjusted if necessary within the range specified above using an inorganic or organic acid such as hydrochloric acid, sulfuric acid, acetic acid, malic acid as well as an alkali solution such as sodium hydroxide, urea, calcium carbonate, ammonia and the like.

The column employed in the present invention may be any column employed ordinarily for purifying a chemical substance.

The quantity of a weak acid ion exchange resin employed in the present invention may readily be selected by those skilled in the art depending on the type of the basic amino acid to be purified and the pH of the culture fluid to be loaded, and may be 1 to 2 times that of the culture fluid when the basic amino acid concentration of the culture fluid is about 10%.

In the method of the present invention, a culture containing a basic amino acid and microbial cells is charged onto the top, i.e., to the upper layer in the column bed, of a column filled with a weak acid cation exchange resin whose particle size is 300 μm or more.

The flow rate is preferably 0.3 to 10 m/h, more preferably 0.5 to 7 m/h as a linear velocity.

After the passing the culture through the column, an eluent is charged preferably continuously onto the top of the column, i.e., onto the column bed to elute the basic amino acid, whereby separating and purifying the basic amino acid.

While the eluent employed in the present invention is not subjected to any limitation with respect to the type and the concentration as long as it is a solution capable of elute the basic amino acid binding to the weak acid ion exchange resin, it may for example be an alkaline aqueous solution such as aqueous ammonia solution or sodium hydroxide solution at a concentration of 0.2 to 6 mol/L, more preferably 0.5 to 3 mol/L.

The flow rate of the eluent as a linear velocity is preferably 0.3 to 10 m/h, more preferably 0.5 to 7 m/h.

The basic amino acid separated and purified as described above can further be purified by means such as decoloration, concentration, and crystallization.

The weak acid ion exchange resin in the column after eluting the basic amino acid can be used repetitively in the method of the present invention only by forcing the eluent to go out of the column by pouring water into the column from the top thereof without conducting any particular resin regenerating procedure.

The present invention is further described in detail in the following Examples, which is not intended to limit the invention.

Example 1

Purification of L-Arginine 200 mL of a culture containing 90 g/L of L-arginine, 8 g/L of citrulline, 1 g/L of glutamic acid, 3 g/L of magnesium sulfate, 10 g/L of sodium chloride, 3 g/L of sodium sulfate and 18 g on a wet basis of a microorganism belonging to the genus *Corynebacterium* was adjusted at pH5.0 using sulfuric acid, and charged at the linear velocity of 1.0 m/h at 45° C. onto a column filled with 200 mL of a weak acid cation exchange resin WK40 (Mitsubishi Chemical Corporation) which had been sieved to remove particles having particle sizes less than 420 μm, to thereby adsorb L-arginine. Then, 200 mL of water was poured into the column to force the culture remaining in the column to go out, and then L-arginine was eluted using a 2.5 mol/L aqueous ammonia solution at the linear velocity of 1.0 m/h. A 140 to 280 ml-volume fraction after starting elution was recovered as a main fraction and then a 280 to 480 ml-volume fraction was recovered as a sub-fraction. As for L-arginine contained in the combination of the main fraction and the subtraction, the yield was 98%, the pigment removal rate was 96% and the cell removal rate was 99%.

Example 2

Purification of L-Ornithine 200 mL of a culture containing 120 g/L of L-ornithine, 8 g/L of citrulline, 1 g/L of glutamic acid, 3 g/L of magnesium sulfate, 10 g/L of sodium chloride, 3 g/L of sodium sulfate and 12 g on a wet basis of a microorganism belonging to the genus *Corynebacterium* was adjusted at pH6.0 using sulfuric acid, and charged at the linear velocity of 1.0 m/h at 45° C. onto a column filled with 200 mL of WK40 which had been sieved to remove particles having particle sizes less than 420 μm, to thereby adsorb L-ornithine. Then, 200 mL of water was poured into the column to force the culture remaining in the column to go out, and then L-ornithine was eluted using a 2.5 mol/L aqueous ammonia solution at the linear velocity of 1.0 m/h. A 140 to 280 ml-volume fraction after starting elution was recovered as a main fraction and then a 280 to 480 ml-volume fraction was recovered as a sub-fraction. As for L-ornithine contained in the combination of the main fraction and the subtraction, the yield was 98%, the pigment removal rate was 96% and the cell removal rate was 99%.

Example 3

Purification of L-Lysine 200 mL of a culture containing 100 g/L of L-lysine, 10 g/L of sodium chloride, 3 g/L of sodium sulfate and 20 g on a wet basis of a microorganism of genus *Corynebacterium* was adjusted at pH6.0 using sulfuric acid, and charged at the linear velocity of 1.0 m/h at 25° C. onto a column filled with 200 mL of a weak acid cation exchange resin MAC-3 (Dow Chemical Company) which had been sieved to remove particles having particle sizes less than 420 μm, to thereby adsorb L-lysine. Then, 200 mL of water was poured into the column to force the culture remaining in the column to go out, and then L-lysine was eluted using a 2.0 mol/L aqueous ammonia solution at the linear velocity of 1.0 m/h. A 140 to 280 ml-volume fraction after starting elution was recovered as a main fraction and then a 280 to 380 ml-volume fraction was recovered as a sub-fraction. As for L-lysine contained in the combination of the main fraction and the subtraction, the yield was 98%, the pigment removal rate was 97% and the cell removal rate was 99%.

Comparative Example 1

Purification of L-Arginine (1)

200 mL of the culture employed in Example 1 was adjusted at pH1.5 using sulfuric acid, and charged at the linear velocity of 1.0 m/h at 45° C. onto a column filled with 200 mL of a strong acid cation exchange resin SK1B (Mitsubishi Chemical Corporation) whose particle size had not been adjusted by sieving, but the column was occluded after charging at the time when 80 mL was passed through the column.

Comparative Example 2

Purification of L-Arginine (2)

200 mL of the culture employed in Example 1 was adjusted at pH1.5 using sulfuric acid, made free of cells by centrifugation, and charged at the linear velocity of 1.0 m/h at 45° C. onto a column filled with 200 mL of a strong acid cation exchange resin SK1B whose particle size had not been adjusted by sieving, to thereby adsorb L-arginine. Then, 200 mL of water was poured into the column to force the culture remaining in the column to go out, and then L-arginine was eluted using a 2 mol/L aqueous ammonia solution at the linear velocity of 1.0 m/h. A 180 to 380 ml-volume fraction after starting elution was recovered as a main fraction and then a 380 to 480 ml-volume fraction was recovered as a sub-fraction. As for L-arginine contained in the combination of the main fraction and the subtraction, the yield was 98% and the pigment removal rate was 62%.

INDUSTRIAL APPLICABILITY

According to the present invention, a basic amino acid can efficiently be purified from a culture containing said basic amino acid and microbial cells.

The invention claimed is:

1. A method for separating and purifying a basic amino acid from a culture comprising the amino acid, which comprises
   (i) obtaining a weak acid cation exchange resin which has been sieved to retain particles which do not pass through a sieve with of a mesh size of 300 μm,
   (ii) allowing a culture comprising a basic amino acid and microbial cells to be charged onto the top of a column filled with said resin whose particle size is 300 μm or more and pass therethrough, and
   (iii) thereafter allowing an eluent to pass through the column,
to thereby separate and purify the basic amino acid.

2. The method according to claim 1, wherein the pH of the culture comprising the basic amino acid and the microbial cells is 4 to 10.

3. The method according to claim 1 or 2, wherein the basic amino acid is arginine, lysine or ornithine.

4. A method for separating and purifying a basic amino acid from a culture comprising the amino acid, which consists of allowing a culture comprising a basic amino acid and microbial cells to be charged onto the top of a column filled with a weak acid cation exchange resin whose particle size is 300 μm or more and pass therethrough, and thereafter adding an eluent onto the top of the column and allowing said eluent to pass through the column, to thereby separate and purify the basic amino acid.

5. The method according to claim 4, wherein the pH of the culture comprising the basic amino acid and the microbial cells is 4 to 10.

6. The method according to claim 4 or 5, wherein the basic amino acid is arginine, lysine or ornithine.

* * * * *